United States Patent
Nagao

(10) Patent No.: US 12,130,273 B2
(45) Date of Patent: Oct. 29, 2024

(54) WATER SAMPLING DEVICE FOR WATER QUALITY MEASUREMENT

(71) Applicant: KURITA WATER INDUSTRIES LTD., Tokyo (JP)

(72) Inventor: Nobuaki Nagao, Tokyo (JP)

(73) Assignee: KURITA WATER INDUSTRIES LTD., Tokyo (JP)

( * ) Notice: Subject to any disclaimer, the term of this patent is extended or adjusted under 35 U.S.C. 154(b) by 239 days.

(21) Appl. No.: 17/637,452

(22) PCT Filed: Sep. 2, 2020

(86) PCT No.: PCT/JP2020/033201
§ 371 (c)(1),
(2) Date: Feb. 23, 2022

(87) PCT Pub. No.: WO2021/070524
PCT Pub. Date: Apr. 15, 2021

(65) Prior Publication Data
US 2022/0276215 A1 Sep. 1, 2022

(30) Foreign Application Priority Data
Oct. 8, 2019 (JP) .................................. 2019-185355

(51) Int. Cl.
*G01N 33/18* (2006.01)
*G01N 1/14* (2006.01)

(52) U.S. Cl.
CPC ............... *G01N 33/18* (2013.01); *G01N 1/14* (2013.01)

(58) Field of Classification Search
CPC .. G01N 1/02; G01N 1/10; G01N 1/18; G01N 2001/1031; G01N 2001/1043;
(Continued)

(56) References Cited

U.S. PATENT DOCUMENTS 3,362,222 A * 1/1968 Johnson .................... G01N 1/18
73/198
3,369,405 A * 2/1968 Galegar ................. G01N 35/00
73/863.33
(Continued)

FOREIGN PATENT DOCUMENTS

CN 107381665 11/2017
CN 207617927 U * 7/2018
(Continued)

OTHER PUBLICATIONS

Espacenet Machine Translation of CN 207617927 U Which Originally Published on Jul. 17, 2018. (Year: 2018).*
(Continued)

*Primary Examiner* — Robert R Raevis
(74) *Attorney, Agent, or Firm* — JCIPRNET

(57) ABSTRACT

A water sampling device for water quality measurement is capable of changing the sampling amount, the number of sampling container(s), the sampling container type and so on according to the item of water quality measurement. Water in a water system can be sampled into a first container Y1 via a sampling source pipe 1, a manifold 2, and a first sampling pipe 3 and a pump P1 connected to the manifold 2. Water in the water system also can be sampled into a second container Y2 from the manifold 2 via a second sampling pipe 4 and a pump P2. In a case where the detection value(s) of one or more of the sensors S1 to S3 set in the water system exceeds a preset standard value or deviates from a standard range, water to be tested is sampled from the water system.

3 Claims, 1 Drawing Sheet

(58) Field of Classification Search
CPC .... G01N 2001/185; G01N 33/18; G01N 1/14; Y02A 20/152
USPC .............. 73/863.31, 864.51, 863.61, 863.81
See application file for complete search history.

(56) References Cited

U.S. PATENT DOCUMENTS

| | | | | |
|---|---|---|---|---|
| 3,727,464 | A * | 4/1973 | Rutkowski | G01N 1/14 73/864.35 |
| 3,896,673 | A * | 7/1975 | Audouze | G01N 1/18 73/864.34 |
| 3,924,471 | A * | 12/1975 | Singer | G01N 1/18 141/130 |
| 3,974,697 | A * | 8/1976 | Speth | G01N 1/2035 73/863.61 |
| 4,022,059 | A * | 5/1977 | Schontzler | G01N 1/18 73/863.02 |
| 4,454,773 | A * | 6/1984 | Brunner | G01N 1/10 73/863.31 |
| 4,576,054 | A * | 3/1986 | Lalin | G05D 7/03 73/864.34 |
| 4,660,422 | A * | 4/1987 | Eads | G01N 1/14 700/282 |
| 4,704,910 | A * | 11/1987 | Conrad | G01N 1/26 73/863.31 |
| 4,713,772 | A * | 12/1987 | Carlson | G01N 33/1893 422/62 |
| 5,115,686 | A * | 5/1992 | Walker | G01N 1/18 73/863.31 |
| 5,469,751 | A * | 11/1995 | Weiss | G01N 1/16 73/863.33 |
| 5,708,219 | A * | 1/1998 | Scheppers | G01N 1/26 73/863.31 |
| 5,939,330 | A * | 8/1999 | Peterson | F04F 1/06 422/62 |
| 6,178,831 | B1 * | 1/2001 | Dawson | G01N 1/2035 73/863.61 |
| 6,925,895 | B2 * | 8/2005 | Barker | G01N 1/14 73/864.34 |
| 6,976,397 | B2 * | 12/2005 | Widmer | G01N 1/2247 73/863.03 |
| 7,681,436 | B2 * | 3/2010 | Biberger | G01N 33/18 73/61.41 |
| 7,770,476 | B2 * | 8/2010 | Davis | G01N 1/2273 73/864.51 |
| 8,047,086 | B2 * | 11/2011 | Smith | C12Q 1/6834 422/402 |
| 8,286,512 | B1 * | 10/2012 | Selbig | G01N 1/16 73/864.81 |
| 9,606,028 | B2 * | 3/2017 | Detweiller | B64U 10/16 |

FOREIGN PATENT DOCUMENTS

| | | |
|---|---|---|
| JP | H116826 | 1/1999 |
| JP | 2003075405 | 3/2003 |
| JP | 2009192340 | 8/2009 |
| JP | 2015188769 | 11/2015 |
| JP | 2017138280 | 8/2017 |
| TW | I440852 | 6/2014 |
| TW | M488632 | 10/2014 |

OTHER PUBLICATIONS

"International Search Report (Form PCT/ISA/210) of PCT/JP2020/033201", mailed on Nov. 24, 2020, with English translation thereof, pp. 1-4.
"Office Action of Taiwan Counterpart Application", issued on Jun. 28, 2023, with English translation thereof, p. 1-p. 8.

* cited by examiner

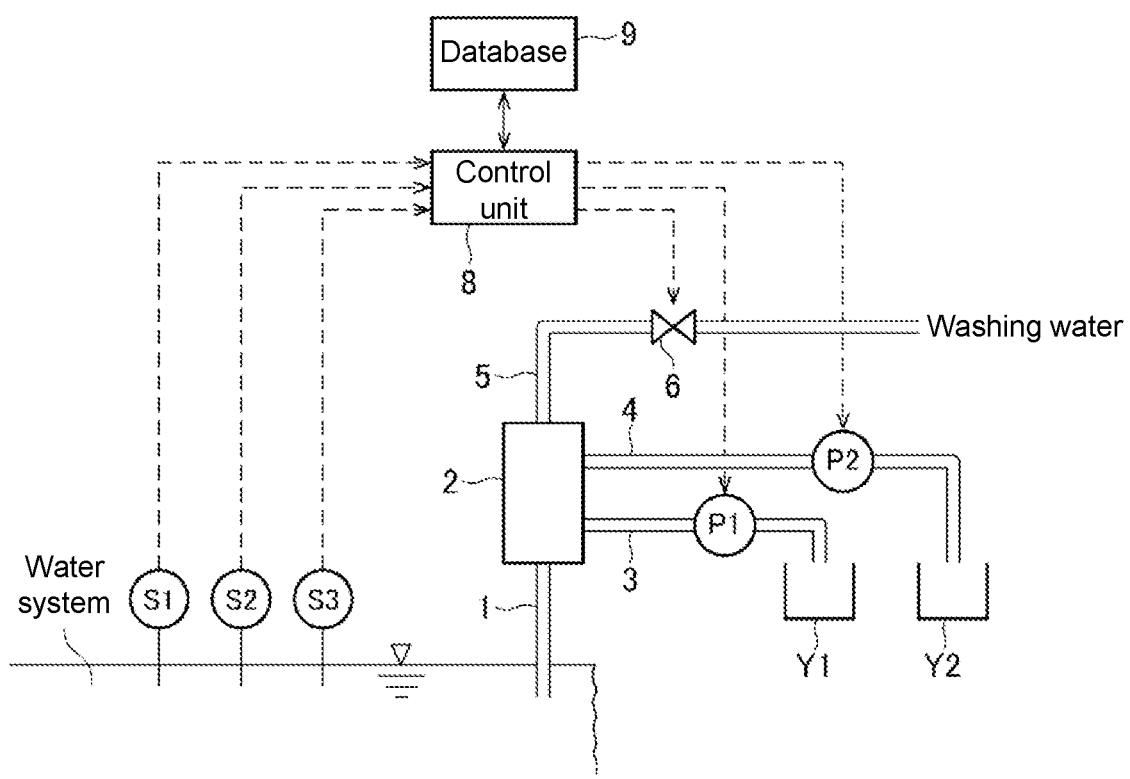

WATER SAMPLING DEVICE FOR WATER QUALITY MEASUREMENT

CROSS-REFERENCE TO RELATED APPLICATION

This application is a 371 application of the International PCT application serial no. PCT/JP2020/033201, filed on Sep. 2, 2020, which claims the priority benefits of Japanese Patent Application No. 2019-185355, filed on Oct. 8, 2019. The entirety of each of the above-mentioned patent applications is hereby incorporated by reference herein and made a part of this specification.

TECHNICAL FIELD

This invention relates to a water sampling device for water quality measurement that is for sampling water to be tested (sample water) from a water system, particularly to a water sampling device that is configured to sample water when an abnormality in water quality is detected by a sensor.

BACKGROUND ART

In the disclosure of Patent Literature 1, water to be tested is continuously flowed in a water quality measuring device from a water system to be measured for water quality, and when an abnormality is detected in the water quality, a part of the tested water is divided and stored in a water sampling tank. That is, the to-be-tested water on occurrence of abnormality is sampled into the water sampling tank.

In the disclosure of Patent Literature 2, the water flowing out of the water quality measuring device is flowed in a water sampling tank subsequently, and after an abnormality in water quality is detected, the water flowing out of the water quality measuring device is bypassed in the water sampling tank. That is, only the to-be-tested water on occurrence of abnormality is remained in the water sampling tank.

CITATION LIST

Patent Literature

Patent Literature 1: Japanese Patent Laid-Open No. H11-6826 (JPH116826A)
Patent Literature 2: Japanese Patent Laid-Open No. 2009-192340 (JP2009192340A)

SUMMARY OF INVENTION

Technical Problem

An object of this invention is to provide a water sampling device for water quality measurement that can change sampling conditions.

An object of this invention in an aspect thereof is to provide a water sampling device for water quality measurement that can change the sampling amount, the number of sampling container(s), the sampling container type and so on according to the item of water quality measurement.

Solution to Problem

The water sampling device for water quality measurement of this invention samples water to be tested from a water system via a sampling line, and has a control means that starts a water sampling action based on a signal from a water quality measuring sensor set in the water system, wherein sampling conditions are changeable.

In an aspect of this invention, the control means is configured to start the water sampling action in a case where a detected value of the sensor exceeds a preset predetermined value or deviates from a predetermined range.

In an aspect of this invention, the water sampling device includes a storage means that stores at least the detected value of the sensor and the sampling time point of the water to be tested.

In an aspect of this invention, the water sampling device has a washing means that supplies washing water to the sampling line.

In an aspect of this invention, the control means controls a washing time period of using the washing means according to the water quality of the water system.

In an aspect of this invention, the sampling line is equipped with a water conveying means that is capable of conveying water in a direction of taking out the water to be tested from the water system and conveying water in an opposite direction.

Advantageous Effects of Invention

The water sampling device for water quality measurement of this invention samples is capable of changing sampling conditions.

In an aspect of this invention, the sampling amount, the number of the sampling container(s), the sampling container type and so on can be changed according to the item of water quality measurement.

BRIEF DESCRIPTION OF DRAWINGS

FIGURE is a block diagram showing the configuration of the water sampling device for water quality measurement according to an embodiment of this invention.

DESCRIPTION OF EMBODIMENTS

This invention will be described in details below referring to FIGURE.

Water in a water system can be sampled into a first container Y1 via a sampling source pipe 1, a manifold 2, and a first sampling pipe 3 and a pump P1 connected to the manifold 2. Water in the water system also can be sampled into a second container Y2 from the manifold 2 via a second sampling pipe 4 and a pump P2. Although not shown in the figure, water in the water system may also be sampled into a third or later container via a third or later sampling pipe. The respective sampling pipes 3 and 4 are connected to the manifold 2 not at the upper part but at, for example, a side face thereof. The upper end of the sampling source pipe 1 is connected to the bottom of the manifold 2, and the lower end of the same is immersed in the water system.

The pumps P1 and P2 are pumps capable of reversing the water conveying direction, such as tube pumps. The sampling pipe may be one equipped with a valve mechanism that can switch the water conveying direction by switching the valve.

Washing water can be introduced to the upper part of the manifold 2 via a pipe 5 and a valve 6.

A plurality of sensors S1, S2 and S3 are set in the water system, their detection signals are input in the control unit 8, and the pumps P1 and P2 and the valve 6 are controlled by the control unit 8. The number of the sensors may alternatively be 2, or 4 or more.

The control unit 8 is connected with a database 9 in a manner such that data can be transmitted and received. The detection value of each sensor is transmitted to the database 9 via the control unit 8 and stored.

The sensors S1 to S3 are exemplified as sensors detecting electrical conductivity, pH, turbidity, ORP (oxidation-reduction potential), color, humidity, water level, data corresponding to agglomeration state (for example, floc diameter, and distance from water surface to sediment layer interface, etc.), and presence or absence of pitch in papermaking process, but are not limited thereto.

In the water sampling device for water quality measurement, sampling of water to be tested from the water system is performed in a case where the detection value(s) of one or more of the sensors S1 to S3 exceed a preset standard value or deviate from a standard range.

In the water sampling device for water quality measurement, washing of the source pipe 1, the manifold 2 and the sampling pipes 3 and 4 is performed when the device is started or after a precedent sampling is finished in the device having been started.

The washing is performed in response to a signal from the control unit 8. First, the valve 6 is opened, clean washing water is supplied into the manifold 2, and the manifold 2 and the source pipe 1 are filled up by the clean washing water.

Moreover, the pumps P1 and P2 are operated normally to pass the washing water in the manifold 2 to the sampling pipes 3 and 4 (the containers Y1 and Y2 are not arranged in the washing time period). By maintaining this state for a predetermined time period, the manifold 2, the source pipe 1 and the sampling pipes 3 and 4 are cleaned, so the valve 6 is closed and the pumps P1 and P2 are stopped. This state is maintained until the sampling begins. In this state, the source pipe 1, the manifold 2 and the sampling pipes 3 and 4 are filled up by the clean washing water.

Further, the washing time period can be set according to the water quality of the water system or the like to perform the washing without excess or insufficiency.

After the washing is finished, the sampling containers Y1 and Y2 are arranged under the tips of the sampling pipes 3 and 4, respectively. The containers have been numbered in advance, and the container numbers and the numbers of the arranged sampling pipes are registered in the database 9. The volumes of the respective containers Y1 and Y2 may also be registered in the database 9.

In a case where the output value(s) of one or more of the sensors S1 to S3 show an abnormality, sampling of water to be tested is performed.

In addition, whether or not the sensor detection value is abnormal can be judged by judging whether or not the sensor detection value exceeds a preset value or deviates from a preset range, whether or not the sensor detection value changes in a rate over a predetermined change rate, or, whether or not the sensor detection value hardly changes for a predetermined time period or a longer time period (i.e., whether or not the sensor is frozen), etc., but is not limited to be judged in these ways.

While the sampling begins, the pumps P1 and P2 are operated reversely. Thereby, air is sent into the manifold 2 from the tips of the sampling pipes 3 and 4 to discharge the water in the sampling pipes 3 and 4, the manifold 2 and the source pipe 1 to the water system.

Thereafter, one or both of the pumps P1 and P2 are operated normally to suck water from the water system and thus sample water to one or both of the containers Y1 and Y2.

If the data of the volumes of the respective containers Y1 and Y2 are registered in the database 9 in advance, it is also possible to set the operation time periods of the respective pumps P1 and P2 according the volumes of the containers and supply, from the water system toward the containers, water to be tested in only an amount of a predetermined multiple of the container volume.

In an example of this invention, firstly, only the pump P1 is operated normally for a sufficient time period such that water overflows from the container Y1, so as to sample water into the container Y1, and then the pump P1 is stopped. In a case where a larger amount of sample water is required, the pump P2 is operated similarly to sample water to be tested into the container Y2. For example, when the electrical conductivity of water with low electrical conductivity is to be measured, water is sampled to two or more containers to sample a large amount of water to be test.

Although only two sampling pipes 3 and 4 are arranged in FIGURE, in a case where three or more sampling pipes are arranged, if required, water is sampled in a similarly manner to the third or later container via the third or later sampling pipe.

In another example of this invention, light-blocking container(s) is/are used as a part or all of the containers. The to-be-tested water sampled in the light-blocking container(s) is used for analysis of photodegradable components.

In another example of this invention, container(s) in which a stabilizer is placed in advance is/are used as a part or all of the containers.

In this invention, it is also possible that sampling is performed using a container at different locations.

In this invention, in a case where samples for a pregiven purpose are characterized in color, it is also possible to identify the color of a drainage using a color sensor and perform sampling according to the conditions (sampling vial, number of samples and so on) preset for each drainage color.

When change in production conditions is known in advance according to a production plan of a factory, etc., it is also possible to change the timing of water sampling according to the date and the time, and to change the number of water samples to be sampled to sample a required amount of water according to the analysis item.

In this invention, in addition to the sensor where abnormality occurs, the time point when abnormality occurs, and the number of the container for sampling water to be tested when abnormality occurs, the water sampling amount is preferably registered in the database 9. It is preferred to further register, in the database, various management information such as the target water system, the name of the water system facility, and the data of the water treatment equipment installed in the water system.

The above embodiment is just an example of this invention, and this invention is not limited thereto.

Although this invention has been described in details with specific aspects, one of ordinary skill in the art should know that various modifications are possible without deviating from the intention and the scope of this invention.

REFERENCE SIGNS LIST

1: Sampling source pipe
2: Manifold

3: First sampling pipe
4: Second sampling pipe
8: Control unit

The invention claimed is:

1. A water sampling device for water quality measurement, which
    samples water to be tested from a water system via a sampling line,
    has a control means that starts a water sampling action based on a signal from a water quality measuring sensor set in the water system, wherein sampling conditions are changeable, and
    has a washing means that supplies washing water to the sampling line,
    wherein the control means controls a washing time period of operating the washing means according to water quality of the water system, and the sampling line is equipped with a water conveying means that is capable of conveying water in a direction of taking out the water to be tested from the water system and conveying water in an opposite direction.

2. The water sampling device of claim 1, wherein the control means is configured to start the water sampling action in a case where a detected value of the sensor exceeds a preset predetermined value or deviates from a predetermined range.

3. The water sampling device of claim 2, which includes a storage means that stores at least the detected value of the sensor and a sampling time point of the water to be tested.

* * * * *